United States Patent
Takahashi et al.

(10) Patent No.: US 9,123,098 B2
(45) Date of Patent: Sep. 1, 2015

(54) MEDICAL IMAGE PROCESSING DEVICE AND MEDICAL IMAGE PROCESSING METHOD, APPLYING WEIGHTED PENALTY TERM IN ITERATIVE APPROXIMATION

(75) Inventors: Hisashi Takahashi, Tokyo (JP); Koichi Hirokawa, Tokyo (JP); Taiga Goto, Tokyo (JP); Yoshiaki Sugaya, Tokyo (JP)

(73) Assignee: HITACHI MEDICAL CORPORATION, Tokyo (JP)

( * ) Notice: Subject to any disclaimer, the term of this patent is extended or adjusted under 35 U.S.C. 154(b) by 52 days.

(21) Appl. No.: 14/112,276

(22) PCT Filed: Apr. 4, 2012

(86) PCT No.: PCT/JP2012/059136
§ 371 (c)(1),
(2), (4) Date: Oct. 17, 2013

(87) PCT Pub. No.: WO2012/147471
PCT Pub. Date: Nov. 1, 2012

(65) Prior Publication Data
US 2014/0226887 A1  Aug. 14, 2014

(30) Foreign Application Priority Data
Apr. 28, 2011  (JP) ................................ 2011-100571

(51) Int. Cl.
*G06K 9/00* (2006.01)
*G06T 7/00* (2006.01)
(Continued)

(52) U.S. Cl.
CPC .............. *G06T 7/0012* (2013.01); *A61B 6/032* (2013.01); *A61B 6/5205* (2013.01); *A61B 6/5258* (2013.01); *G06T 5/002* (2013.01); *G06T 11/006* (2013.01); *A61B 6/583* (2013.01); *G06T 2207/10081* (2013.01); *G06T 2207/20182* (2013.01); *G06T 2207/30004* (2013.01); *G06T 2211/424* (2013.01)

(58) Field of Classification Search
None
See application file for complete search history.

(56) References Cited

U.S. PATENT DOCUMENTS 5,909,476 A * 6/1999 Cheng et al. ...................... 378/4
2007/0297660 A1* 12/2007 Hsieh et al. ................... 382/131
(Continued)

FOREIGN PATENT DOCUMENTS

| JP | 60-17568 | 1/1985 |
| JP | 2009-540966 | 11/2009 |
| JP | 2010-136958 | 6/2010 |
| WO | WO 2010-062956 A1 | 6/2010 |

OTHER PUBLICATIONS

International Search Report in PCT/JP2012/059136, Jan. 11, 2012.
(Continued)

*Primary Examiner* — Tahmina Ansari
(74) *Attorney, Agent, or Firm* — Cooper & Dunham LLP

(57) ABSTRACT

With respect to projection data covering a plurality of sites, in order to create a medical image in which a uniform noise reduction effect is achieved for all sites within the projection data, an arithmetic device (5) determines one or more of proper subsets on the basis of scanning conditions and reconstruction conditions (step 2). Next, the arithmetic device (5) calculates a penalty-term weight for each proper subset on the basis of a detector output weight corresponding to a set element contained in the proper subset (step 3). Then, the arithmetic unit (5) performs an iterative approximation by using the penalty-term weight for each proper subset (step 4).

10 Claims, 8 Drawing Sheets

(51) Int. Cl.
  *A61B 6/03* (2006.01)
  *A61B 6/00* (2006.01)
  *G06T 5/00* (2006.01)
  *G06T 11/00* (2006.01)

(56) References Cited

U.S. PATENT DOCUMENTS

| | | | |
|---|---|---|---|
| 2008/0253502 A1* | 10/2008 | Ziegler et al. | 378/4 |
| 2008/0273778 A1* | 11/2008 | Goto et al. | 382/131 |
| 2010/0128958 A1* | 5/2010 | Chen et al. | 382/132 |
| 2011/0052023 A1* | 3/2011 | Garg et al. | 382/131 |
| 2011/0091007 A1* | 4/2011 | Betcke et al. | 378/4 |
| 2013/0177132 A1* | 7/2013 | Takahashi et al. | 378/4 |
| 2014/0226887 A1* | 8/2014 | Takahashi et al. | 382/131 |

OTHER PUBLICATIONS

Taiga Goto et al., "Chikuji Kinji Saikosei Algorithm no Kaihatsu", Japanese Society of Radiological Technology Sokai Gakujutsu Taikai Yokoshi, Feb. 25, 2011, vol. 67, 184.

J. Wang et al., "Multiscale Penalized Weighted Least-Squares Sinogram Restoration for Low-Dose X-Ray Computed Tomography", Conf. Proc. IEEE Eng. Med. Biol. Soc., 2008, vol. 55, issue 5, 1022-1031.

H.R. Shi et al., "Quadratic Regularization Design for 2-D CT", IEEE Trans. Med. Img., 2009, vol. 28, No. 5, 645-656.

Z. Tian et al., "Low-Dose CT Reconstruction via Edge-Preserving Total Variation Regularization", Phys. Med. Biol., 2011, vol. 56, No. 18, 5949-5967.

* cited by examiner

MEDICAL IMAGE PROCESSING DEVICE AND MEDICAL IMAGE PROCESSING METHOD, APPLYING WEIGHTED PENALTY TERM IN ITERATIVE APPROXIMATION

FIELD OF THE INVENTION

The present invention relates to a medical image processing device and the like which perform a correction process and/or reconstruction process of projection data using the iterative approximation method that includes the weight in accordance with the output of a detector and the penalty term in an evaluation function.

DESCRIPTION OF RELATED ART

An X-ray CT apparatus comprises an X-ray detector in which detection elements are arrayed in the channel direction and the row direction. In a scanning by an X-ray CT apparatus, by revolving an X-ray tube and an X-ray detector that are facing each other around an object to be examined, projection data sets are collected in discrete positions of the X-ray tube in the revolving direction (which also are the positions of the facing X-ray detector). In the following description, an acquisition unit of projection data in the respective X-ray tube positions will be referred to as a "view". After projection data is collected, an arithmetic device acquires filtered projection data by superimposing a reconstruction filter in the channel direction of the projection data for each view and each row, then performs back projection with respect to the acquired filtered projection data while being weighted in the view direction, so as to create a cross-sectional image as the distribution map of the X-ray attenuation coefficient inside of the object in a non-destructive manner. In the following description, the method for creating a cross-sectional image from projection data will be referred to as the "image reconstruction method", and an image obtained by the image reconstruction method will be referred to as a CT image.

The image reconstruction method is roughly divided into an analytical method and an iterative approximation method. The analytical method analytically solves a problem based on the projection cross-sectional theorem. The iterative approximation method models the observing system which achieves the acquisition of projection data mathematically, and estimates the best image using the iterative method on the basis of the mathematical model.

By comparison, the advantage of the analytical method is a predominantly smaller amount of calculation since reconstruction images can be directly obtained from the projection data. On the other hand, the advantage of the iterative method is that artifacts (cone beam artifacts, etc.) or quantum noise on an image to be generated in the analytical method can be reduced since physical processes for achieving projection data acquisition or statistical fluctuation included in projection data can be considered respectively as a mathematical model or a statistical model.

As the image reconstruction method in a multi-slice CT, the analytical method such as the Feldkamp method or the improved version of Feldkamp method have mainly been used on the ground of a small amount of calculation. However, with recent technical advancement of computers, practical use of the iterative approximation method has also been considered. In particular, a technique for improving the image quality by the iterative approximation method has been proposed.

Here, the iterative approximation method is roughly divided into the following two kinds by the difference of estimated variables.

(1) The method for constructing an evaluation function by setting the projection value of projection data as the variable.

(2) The method for constructing an evaluation function by setting the pixel value of image data as variables.

The method (1) is applied to processes such as correction of projection data to perform in prior to an image reconstruction process. In the following description, the correction of projection data to which the iterative approximation method of (1) is applied will be referred to as an "iterative approximation projection data correcting process".

The method of (2) is applied to an image reconstruction process. In the following description, the image reconstruction process to which the iterative approximation method of (2) is referred to as an "iterative approximation reconstructing process".

In the iterative approximation projection data correcting process, the assessment index of projection data is set in advance, and the projection data is iteratively updated so that the evaluation value which is the numerical conversion of an assessment index takes the maximum value or the minimum value. As for the evaluation index, inconsistency between interim image data which is to be updated and the measured projection data or probabilistic plausibility is to be used. As an example, the iterative approximation projection data correcting process has been proposed in Non-patent Document 1, which uses the penalized weighted square error function which is expressed by the following equation as the evaluation function.

[Equation 1]

$$\Phi(p) = \sum_{i=1}^{I} d_i(y_i - p_i)^2 + \beta \sum_{i=1}^{I} \sum_{k \in \kappa_i} v_{ik} \psi(p_i - p_k) \quad (1)$$

In the equation (1), 1, ..., i, ..., I are serial numbers for uniquely specifying combination of a channel of a detector, a row of the detector and a view. $P_i$ and $y_i$ are the interim projection data and measured projection data to be specified by serial number i respectively. $P = \{p_1, \ldots p_i, \ldots p_I\}$ indicates vectors of the interim projection data. $\kappa_i$ is a set of detection elements in the vicinity of the detection element specified by serial number i.

$v_{ik}$ is a constant which indicates the correlativity between the detection element specified by serial number i and the detection element specified by serial number k. In Non-patent Document 1, $v_{ik}$ is empirically determined.

$\Psi(p_i - p_k)$ is a potential function in which the contrast between interim projection data $p_i$ and interim projection data $p_k$ is set as a variable. In Non-patent Document 1, a quadratic function is used as the potential function.

$d_i$ is the weighted coefficient to be weighted on the difference value between the measured projection data $y_i$ and the forward projection data. Since $d_i$ in image processing of CT images is the value which reflects detector output of the detection element specified by serial number i, $d_i$ will be referred to as "detector output weight" in the following description. The detector output is the value which is dependent on the number of detector photons.

β is an arbitrary constant.

In an iterative approximation reconstruction process, an evaluation index of image data is set in advance, and the image data is iteratively updated so that the evaluation value which is numerical conversion of the assessment index takes the maximum value or the minimum value. As for the evaluation index, inconsistency between the forward projection data in which interim image data is converted into projection data in an updating process and the measured projection data or probabilistic plausibility is to be used. As an example, the iterative approximation reconstruction process has been proposed in Non-patent Document 2, which uses the penalized weighted square error function which is expressed by the following equation as the evaluation function.

[Equation 2]

$$\Phi(x) = \sum_{i=1}^{I} d_i \left( y_i - \sum_{j=1}^{J} a_{ij} x_j \right)^2 + \beta \sum_{j=1}^{J} \sum_{k \in X_j} w_{jk} \psi(x_j - x_k) \quad (2)$$

In the equation (2), 1, ... j, ..., J are serial numbers for uniquely specifying the pixels in image data (two-dimensional coordinates). $X_j$ is the pixel value in the pixel specified by serial number j. $X = \{X_1, \ldots X_j, \ldots, X_J\}$ is a vector which represents image data.

$a_{ij}$ is a matrix element which associates image data with projection data. This matrix represents the characteristic of the scanning system of an X-ray CT apparatus via a mathematical model, and is referred to as a "system matrix".

$X_j$ is a set of pixels that are in the vicinity of the pixel which is specified by serial number j. $W_{jk}$ is a constant indicating the correlativity between the pixel specified by serial number j and the pixel specified by serial number k. In general, $w_{jk}$ is the inverse number of the distance between the central position of the pixel specified by serial number j and the central position of the pixel specified by serial number k.

$\Psi(X_j - X_k)$ is a potential function in which the contrast between pixel value $X_j$ in the pixel to be specified by serial number j and pixel value $X_k$ in the pixel value to be specified by serial number k is set as the variable. In Non-patent Document 2, a quadratic function has been proposed as the simplest potential function. Also, a method which changes the form of potential function by an arbitrary parameter is proposed in Non-patent Document 3.

The other constants are the same as the equation (1).

In the updating equations which are developed from the equation (1) by various numerical analytical approaches, interim projection data $p_i$ in the process of updating is smoothed by the penalty term of the second order according to the contrast from interim projection data $p_k$ in the vicinity while being subjected to the restriction of measured projection data $y_i$ and detector output weight $d_i$ by the first-order term of the equation (1). Therefore, arbitrary constant β of equation (1) is the parameter for adjusting the degree in smoothing of interim projection data $p_i$.

In the same manner, arbitrary constant β in the equation (2) is the parameter for adjusting the degree in smoothing of image data $X_j$.

In Non-patent Document 2 and Non-patent Document 3, arbitrary constant β is a constant throughout the entire iterative approximation reconstructing process.

On the other hand, en approach for changing β is proposed in Non-patent Document 4. When β remains as constant, the spatial resolution and noise reducing performance become inhomogeneous depending on the position of the pixel in a CT image. Thus in Non-patent Document 4, inhomogeneity of spatial resolution and noise reducing performance is mitigated in addition to the contrast of the pixels in the vicinity, by changing β in the respective pixels.

PRIOR ART DOCUMENTS

Non-Patent Documents

Non-patent Document 1: T. Li et. al., "Nonlinear Sinogram Smoothing for Low-DoSe X-ray CT", IEEE, Trans. Nucl. Sci., Vol. 51, No. 5, pp. 2505-2513, 2004

Non-patent Document 2: K. Sauer al., "A Local Update Strategy for Iterative Reconstruction form Projections", IEEE. Trans. Signal. Proc., Vol. 41, No. 2, pp. 534-548, 1993

Non-patent Document 3: J. B. Thibault et. al., A three-dimensional Statistical approach to improved image quality for multislice helical CT", Med. Phys, Vol. 34, No. 11, pp. 4526-4544, 2007

Non-patent Document 4: H. R. Shi et. al., "Quadratic Regularization Design for 2-D CT", IEEE. Trans. Med. Imag., Vol. 28, No. 5, pp 645-656, 2009

Non-patent Document 5: T. Goto et. al., "Weighted-Feldkamp algorithm with Selective narrowest cone angle data for conebeam CT", Proc. Of The Eighth Meeting on Fully Three-dimensional Image Reconstruction in Radiology and Nuclear Medocine, pp. 189-192, 2005

Non-patent Document 6: J. Wang et. al., "Penalized weighted least-Squares approach to Sonogram noise reduction and image reconstruction for low-dose X-ray computed tomography", IEEE. Trans. Med. Imag., Vol. 25, No. 10, pp. 1272-1283, 2006

SUMMARY OF INVENTION

Technical Problem

Upon applying an iterative approximation projection data correcting process or iterative approximation reconstructing process over plural regions (a chest region and an abdominal region, etc.), it is preferable for an observer of CT images that the quantum noise reducing effect and artifact reducing effect (hereinafter referred to as "noise reducing effect" when the two are not distinguished) are performed evenly without depending on a region.

However, when an iterative approximation projection data correcting process or iterative approximation reconstructing process are applied over plural regions, magnitude of detector output weight $d_i$ causes the difference of noise reducing effect among plural regions in a CT image. For example, a case is assumed here in which an iterative approximation method on the basis of the equation (1) or equation (2) is applied to the range from a chest region to an abdominal region. When compared to a chest region which is less affected by X-ray attenuation due to the existence of lungs (hollow organs) and has a large number of elements i with a large value of detector output weight $d_i$, an abdominal region having a small number of elements i with a large value of detector output weight $d_i$ is under less constraint of detector output weight $d_i$ in the equation (1) and equation (2). Therefore, when the same image processing is performed on the chest region and the abdominal region, the noise reducing effects will be different in each region, which leads to generation of undesired CT images for the observer with varied noise reducing effects in different regions.

Also, variability of noise reducing effect among plural regions can be reduced when β is changed in the respective pixels as disclosed in Non-patent Document 4. However, by the homogenization of the magnitude of detector output weight $d_i$, the noise reducing effect in CT images, i.e. reduction of quantum noise and artifacts becomes insufficient. Further, a problem remains in the method disclosed in Non-patent Document 4 that an immense amount of time is required for the process of determining β in the respective pixels.

The objective of the present invention, considering the previously described problems, is to provide a medical image processing device, etc. capable of creating a medical image, with respect to projection data covering plural regions, in which the effect for reducing quantum noise and artifacts is evenly performed in all regions included in the projection data without drastically increasing the amount of calculation.

BRIEF SUMMARY OF THE INVENTION

A first invention for achieving the above-described objective is a medical image processing device which performs projection data correcting process and/or image reconstruction process using an iterative approximation method including the detector output weight which is a weight in accordance with an output of a detector and the penalty term in an evaluation function, comprising:

a proper subject determining unit configured to determine, on the basis of scanning conditions and reconstruction conditions, one or more proper subjects from the universal set of which information for uniquely specifying combination of a channel of the detector, a row of the detector and a view which is the acquisition unit of the projection data is set as a set element;

a penalty-term weight calculating unit configured to calculate for each of the proper subsets the penalty-term weight which is the weight related to the penalty term on the basis of the detector output weight corresponding to the set element included in the proper subset; and an iterative approximation method executing unit configured to execute the iterative approximation method using the penalty-term weight for each of the proper subsets.

A second invention is a medical image processing method which performs the projection data correcting process and/or the image reconstruction process using an iterative approximation method including a detector output weight which is a weight in accordance with an output of a detector and a penalty term in an evaluation function, including:

determining, on the basis of scanning conditions and reconstruction conditions, one or more proper subsets from the universal set of which the information for uniquely specifying combination of a channel of the detector, a row of the detector and a view which is the acquisition unit of the projection data is set as a set element;

calculating for each of the proper subsets a penalty-term weight which is a weight related to the penalty term on the basis of the detector output weight corresponding to the set elements included in the proper subset; and executing the iterative approximation method using the penalty-term weight for each of the proper subsets.

Effect of the Invention

In accordance with the present invention, with respect to projection data covering plural regions, it is possible to create medical images in which the reducing effect of quantum noise and artifacts is evenly achieved in all regions included in the projection data without drastically increasing the amount of calculation.

DESCRIPTION OF REFERENCE NUMERALS

DETAILED DESCRIPTION OF THE INVENTION

An embodiment of the present invention will be described below in detail referring to the attached drawings. First, the configuration of an X-ray CT apparatus will be described referring to FIG. 1 and FIG. 2.

Figure 1:
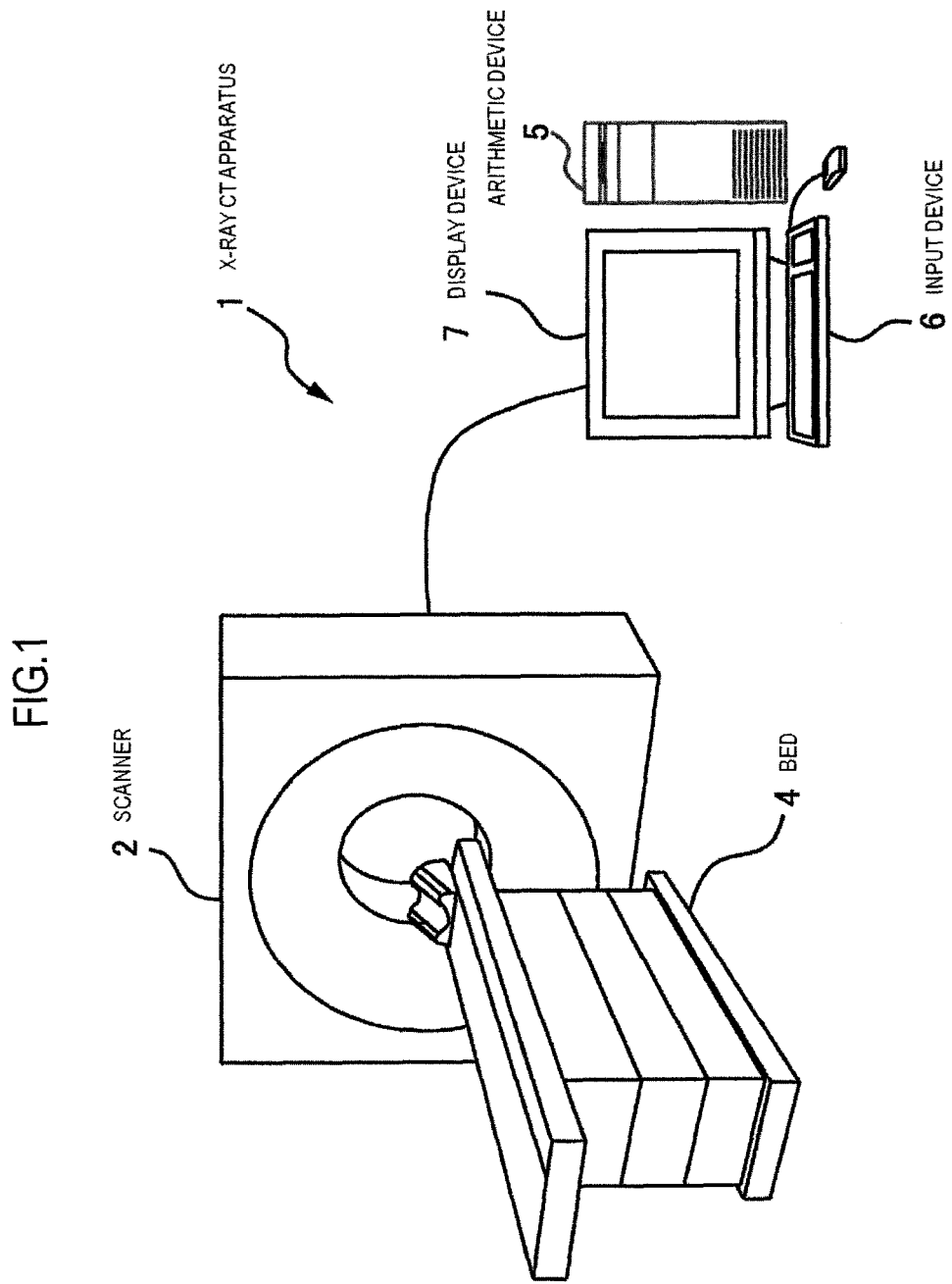
FIG. 1 is an overall external view of an X-ray CT apparatus 1.

As shown in FIG. 1, the X-ray CT apparatus 1 includes devices such as a scanner 2 in which an X-ray tube 11 and detector 12 are mounted, a bed 4 on which an object 10 is placed, an arithmetic device 5 configured to execute processing of data acquired from the detector 12, an input device 6 such as a mouse, a trackball, a keyboard and a touch panel, and a display device 7 configured to display reconstruction images (CT images).

An operator inputs scanning conditions or reconstruction conditions via the input device 6. The scanning conditions include, for example the translation velocity of a bed, tube current, tube voltage, scanning range (the range of the slice position), and scanning view number per revolution. Also, the reconstruction conditions include, for example a region of interest, reconstruction image size (the size of a reconstruction image), and a reconstruction filtering function.

Figure 2:
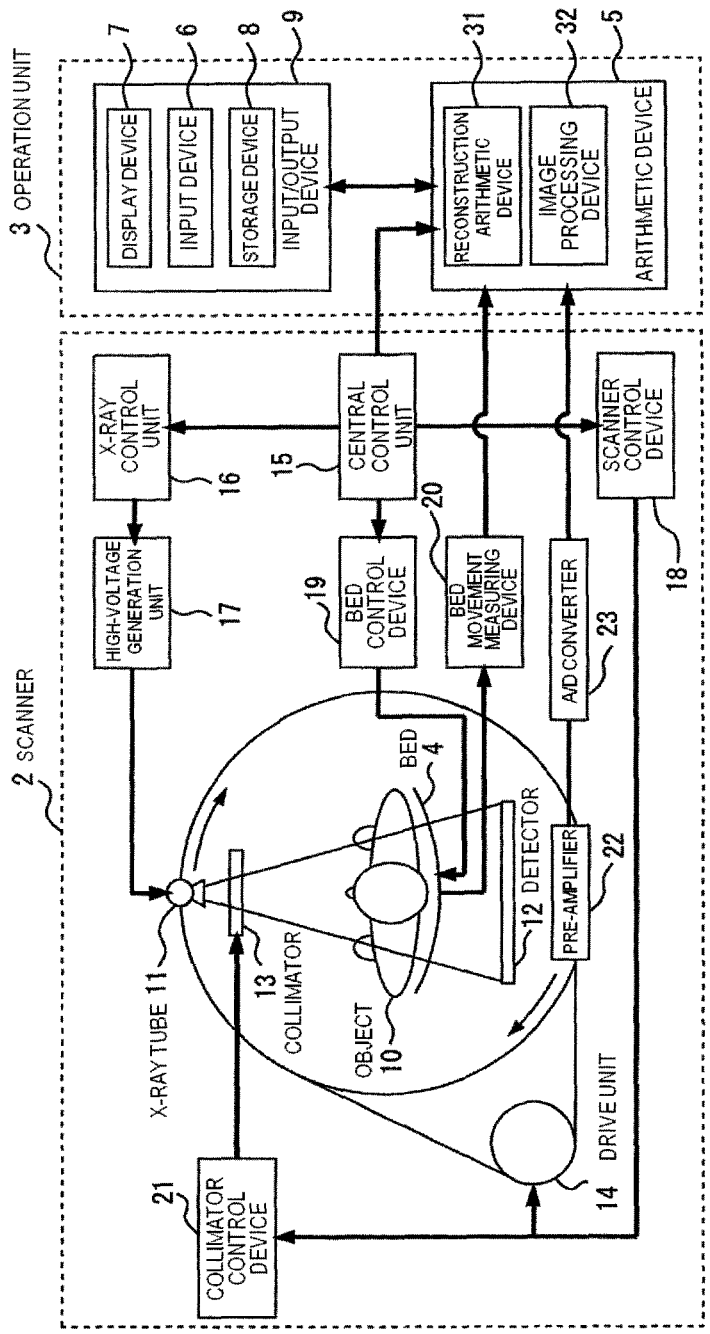
FIG. 2 is a configuration diagram of an X-ray CT apparatus.

As shown in FIG. 2, the X-ray CT apparatus 1 is roughly divided into the scanner 2, an operation unit 3 and the bed 4.

The scanner 2 is configured by devices such as the X-ray tube 11 (X-ray generation device), the detector 12, a collimator 13, a drive device 14, a central control unit 15, an X-ray control unit 16, a high-voltage generation device 17, a scanner control device 18, a bed control device 19, a bed translation measurement device 20, a collimator control device 21, a pre-amplifier 22, and an A/D converter 23.

The central control device 15 inputs scanning conditions or reconstruction conditions from the input device 6 in the operation unit 3, and transmits the control signals necessary for scanning to the collimator control device 21, the X-ray control device 16, the scanner control device 18, and the bed control device 19.

The collimator control device 21 controls the position of the collimator 13 on the basis of the control signals.

When scanning is started by receiving a scanning start signal, the X-ray control device 16 controls the high-voltage generation device 17 on the basis of the control signals. The high-voltage generation device 17 applies a tube voltage and a tube current to the X-ray tube 11 (X-ray generation device). In the X-ray tube 11, an energy electron in accordance with the applied tube voltage is emitted from the cathode, and an X-ray of the energy in accordance with the electronic energy is irradiated to the object 10 by collision of the emitted electron against a target (anode).

Also, the scanner control device 18 controls the drive device 14 based on the control signals. The drive device 14 revolves a gantry unit in which the X-ray tube 11, the detector 12, the preamplifier 22, etc. are mounted around the object 10.

The bed control unit 19 controls the bed 4 based on the control signals.

The X-ray irradiated from the X-ray tube 11 is subjected to control of the irradiation region thereof by the collimator 13, absorbed (attenuated) in accordance with the X-ray attenuation coefficient in each tissue of the object 10, passes through the object 10 to be detected by the detector 12 which is placed at the position opposite from the X-ray tube 11. The detector 12 is formed by plural detection elements placed in the two-dimensional direction (the channel direction and the row direction orthogonal thereto). The X-ray which received light by the respective detection elements is converted into the measured projection data. In other words, the X-ray detected by the detector 12 is converted into a current, amplified by the pre-amplifier 22, converted into digital data by the A/D converter 23, performed with LOG conversion, calibrated and input to the arithmetic device 5 as measured projection data.

At this time, since the X-ray tube 11 and the detector 12 which are facing each other revolve around the object 10, the measured projection data can be understood as the discrete X-ray tube positions (facing detector positions) in the rotational direction. The acquisition unit of measured projection data in the respective X-ray tube positions is a "view".

The arithmetic device 5 is formed by devices such as a reconstruction arithmetic device 31 and an image processing device 32. Also, the input/output device 9 is formed by devices such as the input device 6 (input unit), the display device 7 (display unit) and a storage device 8 (storage unit).

The reconstruction arithmetic device 31 performs an image reconstruction process using measured projection data, and generates a reconstruction image. The reconstruction arithmetic device 31 generates filtered projection data by superimposing a reconstruction filter over the measured projection data of each view, and creates a cross-sectional image in a non-destructive manner as a distribution chart of the X-ray attenuation coefficient inside of the object 10 by performing a back projection process in which the view-direction weighting is implemented on the filtered projection data.

The reconstruction arithmetic device 31 stores the generated reconstruction images in the storage device 8. Also, the reconstruction arithmetic device 31 displays the generated reconstruction image on the display device 7 as a CT image. Or, the image processing device 32 performs the image processing with respect to the reconstruction image stored in the storage device 8, and displays the processed image on the display device 7 as a CT image.

The X-ray CT apparatus 1 is roughly divided into a multi-slice CT which uses the detector 12 in which detection elements are two-dimensionally arrayed and a single-slice CT which uses the detector 12 in which detection elements are arrayed in a row, i.e. in one-dimensional direction (only in the channel direction). In a multi-slice CT, an X-ray beam is irradiated in concert with the detector 12 while being spread in a conical shape or pyramid shape from the X-ray tube 11 which is an X-ray source. In a single-slice CT, a fan-shaped X-ray beam is irradiated from the X-ray tube 11. Generally in scanning by the X-ray CT apparatus 1, irradiation of an X-ray is performed while the gantry unit revolves around the object 10 which is placed on the bed 4 (excluding scanogram imaging).

The scanning mode in which the bed 4 is fixed during scanning and the X-ray tube 11 revolves around the object 10 in a form of circular orbit is referred to as axial scanning. In particular, the scanning mode which repeats scanning while the bed 4 is fixed and moving the bed 4 to the next scanning position is referred to as, for example, step-and-shoot scanning. Since axial scanning can be considered as step-and-shoot scanning in which the bed 4 is moved to a scanning position only one time, the both kinds of scanning will be referred to as step-and-shoot scanning in the following description.

Also, the scanning mode in which the X-ray tube 11 revolves around the object 10 in a helical manner while the bed 4 is translated continually is referred to as helical scanning.

In case of step-and-shoot scanning, the bed control device 19 holds the bed 4 still during scanning. Also in case of spiral scanning, the bed control device 19 translates the bed 4 parallel to the body-axis direction during scanning, in accordance with the bed-feeding velocity which is a scanning condition input via the input device 6.

The X-ray CT apparatus 1 is, for example a multi-slice CT. Also, the scanning method applied to the X-ray CT apparatus 1 is, for example the rotate-rotate method (the third generation).

Next, detector output weight $d_i$ in the equations (1) and (2) will be described referring to FIG. 3 and FIG. 4.

Figure 3:
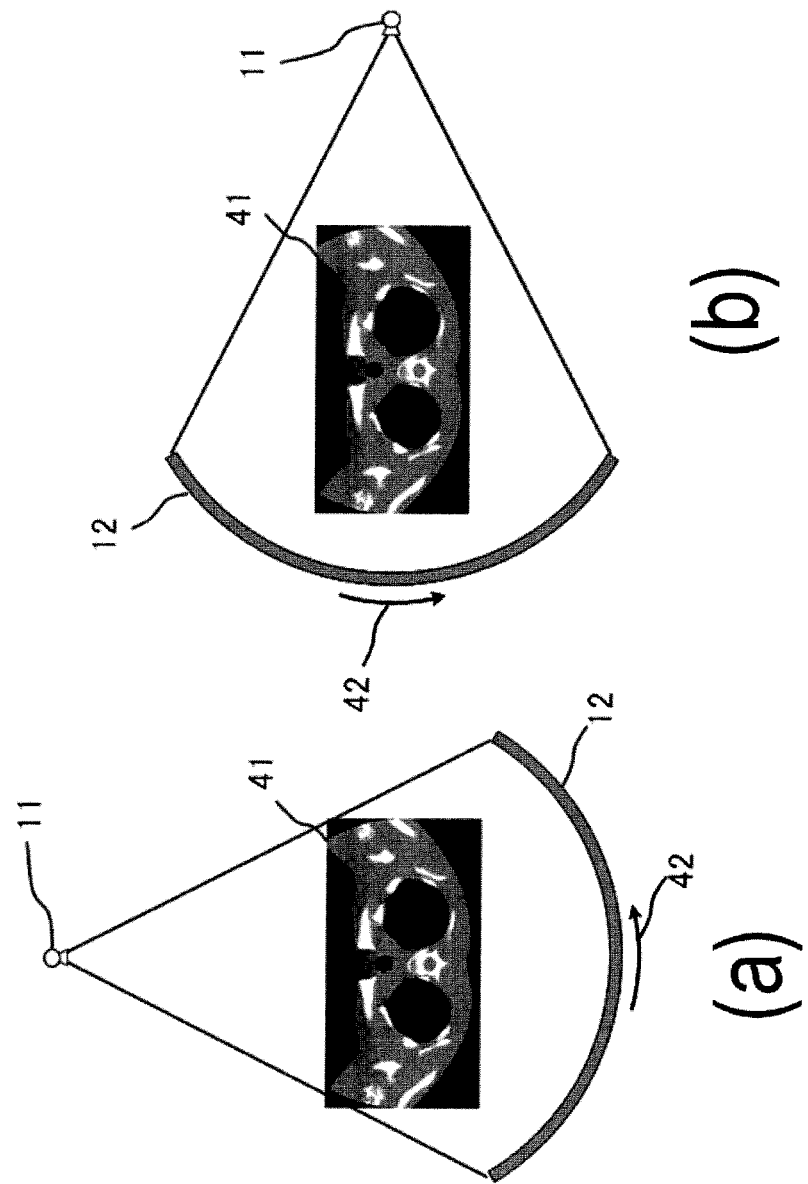
FIG. 3 is a pattern diagram showing a cross-sectional image of shoulder regions in a phantom of a human body as well as the vertical direction view and the horizontal direction view with respect to the cross-sectional image.

FIG. 3 schematically shows a cross-sectional image 41 (CT image) of the shoulder regions in a phantom of a human body which is created by the reconstruction process of the X-ray CT apparatus 1, as well as the vertical-direction view (a) and the horizontal-direction view (b) of the cross-section image 41. In order to provide a simple explanation, only two dimensions of a view and a channel 42 are indicated without considering the dimension of the rows in the detector 12. The horizontal-direction view (b) has a longer path length of an X-ray through a human body compared to the vertical-direction view (a), and has more channels 42 which indicate a small detector output value. In other words, a large amount of noise is included in the detector output in the horizontal-direction view (b). For this reason, streaky artifacts are generated mainly in the horizontal direction in a CT image reconstructed by the image reconstruction method of the analytical approach.

Since detector output weight $d_i$ of the equations (1) and (2) is the value in accordance with the detector output, detector output weight $d_i$ corresponding to the horizontal-direction view (b) is smaller than detector output weight $d_i$ corresponding to the vertical-direction view (a). In other words, the horizontal-direction view (b) relatively receives less restriction by the first-order term in the equations (1) and (2) compared to the vertical-direction view (a), thus receives more smoothing effect by the second-order term (penalty term). Therefore, in the iterative approximation method using the evaluation function such as the equations (1) and (2), the noise included in the detector output can be averaged and streaky artifacts generated in CT images can be effectively reduced. Also by the same principle, the iterative approximation method can effectively reduce quantum noises generated in CT images.

It is preferable that the quantum noise reducing effect and streaky artifact reducing effect (=noise reducing effect) in CT images are evenly provided without depending regions. However, when both iterative approximation processes are applied over plural regions, the difference of degrees in detector output weights $d_i$ causes the difference of noise reducing effects among plural regions in CT images.

Figure 4:
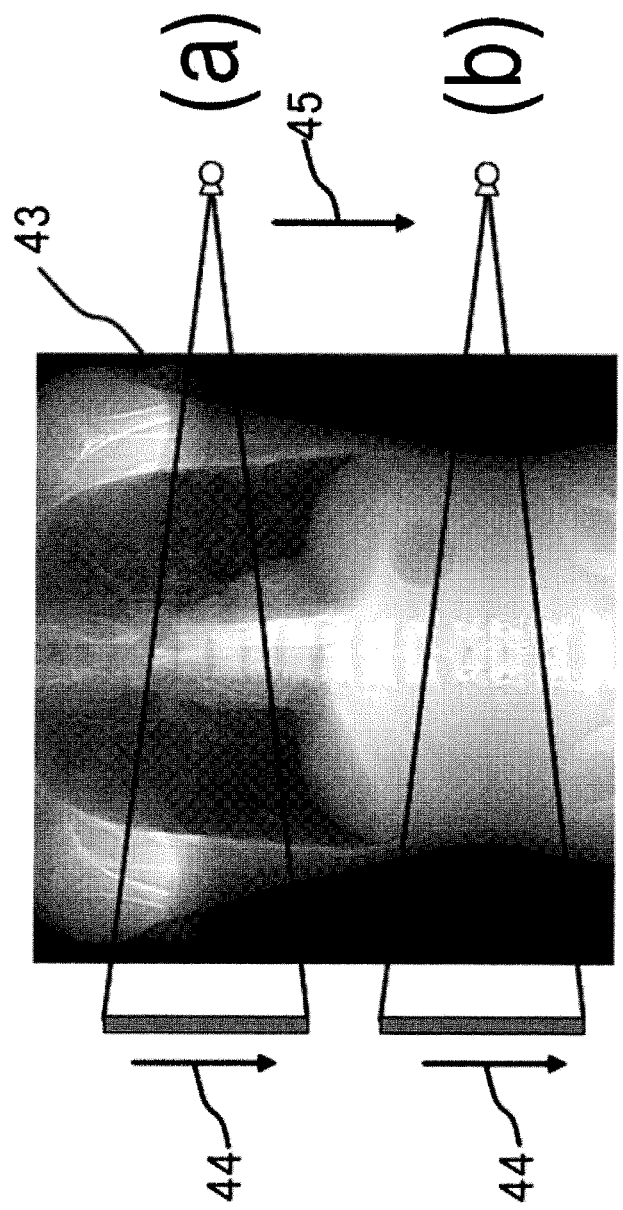
FIG. 4 is a pattern diagram showing a coronal plane image in a phantom of a human body, as well as a view corresponding to a chest region and a view corresponding to an abdominal region in the coronal plane image.

FIG. 4 schematically shows, with respect to a chest region and an abdominal region of a phantom of a human body, a coronal plane image 43 (CT image) created by the X-ray CT apparatus 1 using the reconstruction process, as well as a view range (a) corresponding to the chest region and a view range (b) corresponding the abdominal region in the coronal plane image 43.

In order to provide a simple explanation, only two dimensions of a view and a row 44 are indicated here without considering the dimension of the channels in the detector 12. 45 indicates the scan direction, i.e. the direction which is directly opposite to the direction for translating the bed 4.

As shown in FIG. 4, when the range from the chest region to the abdominal region is imaged by the X-ray CT apparatus 1, the average value of detector outputs in the chest region is greater than the average value of the detector outputs in the abdominal region. This is because the chest region includes lungs (hollow regions) and the attenuation amount of an X-ray is relatively smaller compared to en area such as an abdominal region.

In other words, when the same iterative approximation method is used in an area from a chest region to an abdominal region without depending on a region using the evaluation function such as the equations (1) and (2), the abdominal region provided mostly with detector output weight $d_i$ having a small value receives relatively small restriction of the equations (1) and (2) compared to the chest region provided mostly with detector output weight $d_i$ having a large value. Therefore, in the iterative approximation method using the evaluation functions such as the equations (1) and (2), the reducing effect of streaky artifacts or quantum noises generated in CT images (noise reducing effect) varies depending on a region.

In the medical image processing device of the present invention, such variability of noise reducing effects among plural regions is equalized.

Each step in the medical image processing device of the present invention will be executed after measured projection data is collected. Therefore, the medical image processing device of the present invention can be the arithmetic device 5 included in the X-ray CT apparatus 1 or a general-purpose computer which is not included in the X-ray CT apparatus. Further, the X-ray CT apparatus 1 and the medical image processing device do not necessarily have to be connected via network. For the avoidance of confusion, the arithmetic device will be described as the medical image processing device of the present invention.

In the same manner, an input unit, a display unit and a storage unit comprised by the medical image processing device of the present invention may be an input device 6, a display device 7 and a storage device 8 included in the X-ray CT apparatus 1, as well as a device comprised by a general-purpose computer which is not included in the X-ray apparatus CT 1 or an external device. For the avoidance of confusion, the input device 6, the display device 7 and the storage device 8 will be described below as an input unit, a display unit and a storage unit comprised by the medical image processing device of the present invention.

Also, while the measured projection data is collected in a fan-beam system, it will be assumed that the data is converted into a parallel-beam system in the following description.

Embodiment 1

Embodiment 1 will be described referring to FIG. 5~FIG. 8. In Embodiment 1, a case in which the present invention is applied to the iterative approximation projection data correcting method will be described. The arithmetic device 5 carries out in Embodiment 1 the projection data correcting process using the iterative approximation method in which the detector output weight (the weight in accordance with the output of the detector 12) and the penalty term are included in the evaluation function.

Figure 5:
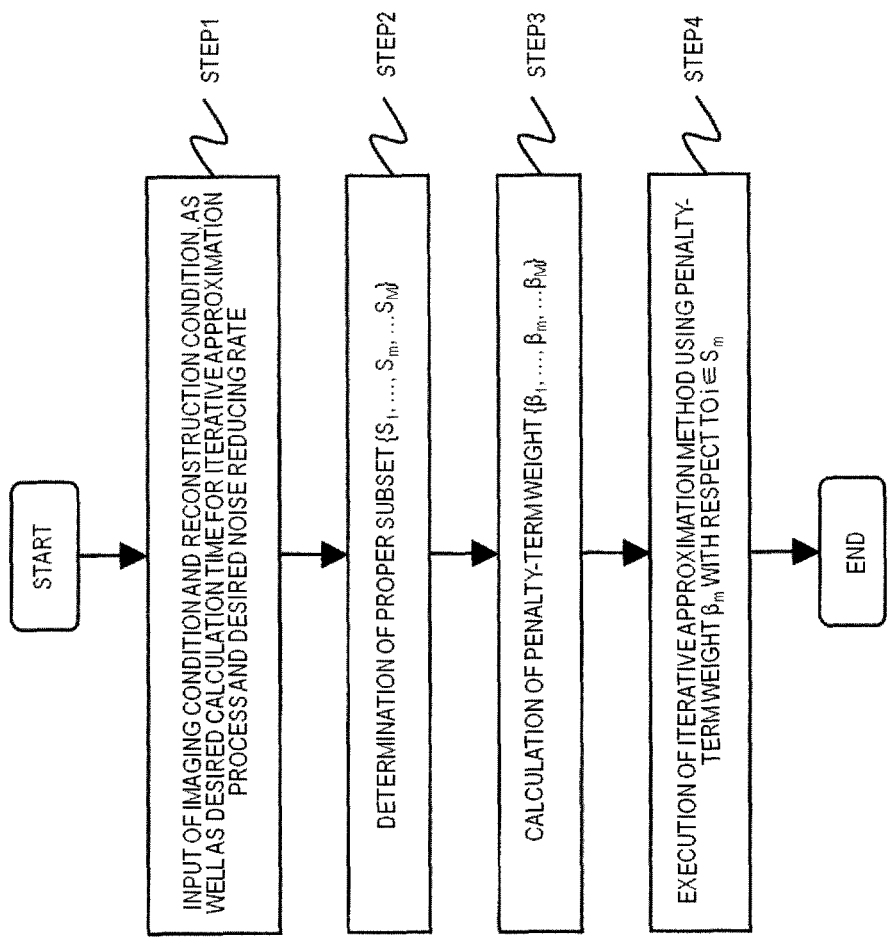
FIG. 5 is a flowchart showing the flow of the overall medical image processing.

As shown in FIG. 5, an operator inputs scanning conditions and reconstruction conditions, as well as a desired calculation time and desired noise attenuation rate of the iterative approximation process (step 1).

As for the scanning conditions, the arithmetic device 5 may automatically set the values stored in the storage device 8 along with the projection data. For example, the arithmetic device 5 may display the values of the scanning condition stored in the storage device 8 on the display device 7, so that all an operator needs to do is to confirm the displayed values.

As for the reconstruction condition, a desired calculation time or desired noise attenuation rate of the iterative approximation process, the arithmetic device 5 may also display the default value or options on the display 7 to support an operator in performing input operation.

For example, the arithmetic device 5 may make the display unit 7 display the options such as "high speed", "middle speed" and "low speed" as the support for inputting desired calculation times. In this case, the arithmetic device 5 stores the calculation time for each option in the storage device 8. Then the arithmetic device 5 sets desired calculation times in accordance with the option selected by the operator.

The arithmetic device 5 may also display the options such as "high image quality", "middle image quality" and "low image quality" on the display unit 7 for supporting the input operation of a desired noise attenuation rate. In this case, the arithmetic device 5 stores in advance the noise attenuation rate for each option in the storage device 8. Then the arithmetic device 5 sets a desired noise attenuation rate in accordance with the option selected by the operator.

Next, the arithmetic device 5 determines one or more proper subsets $\{S_1, \ldots, S_m, \ldots, S_M\}$ on the basis of the scanning condition and reconstruction condition that are input in step 1 (step 2).

Universal set $\Omega$ is provided with serial numbers $\{1, \ldots i, \ldots, I\}$ for uniquely identifying combination of a channel of the detector 12, a row of the detector 12 and a view as a set element. More specifically, when the number of channels in detector 12 is C, the number of rows in detector 12 is R and the number of views in the entire scanning is V, $\Omega = \{1, 2, 3, \ldots, \ldots, C \times R \times V - 2, C \times R \times V - 1, C \times R \times V\}$.

Here, $S_m$ being the proper subset of $\Omega$ means that $S_m \subset \Omega$ ($S_m$ is the subset of $\Omega$) and also that $S_m \neq \Omega$. Further, it will be assumed, with respect to the set $(S_i, S_j)$ of an arbitrary proper subset, that $S_i \cap S_j = \phi$ in the following description.

First, a case of step-and-shoot scanning will be described. In step-and-shoot scanning, it is assumed that the same region is being imaged while the position of the bed 4 is fixed. Then the arithmetic device 5 determines the set elements of the respective proper subsets so that the projection data collected while the position of the bed 4 is fixed belongs to the same proper subset.

In case of step-and-shoot scanning, the number of partitions in universal set $\Omega$ i.e., the number M in proper subset $S_m$ is the same as the number of times that the position of bed 4 is moved.

Here, the number of views to be imaged in the respective positions of the bed 4 is set as $V_1, \ldots, V_m, \ldots, V_M$. In this case, the number of views in an entire scanning is: $V = V_1 + \ldots + V_m + \ldots V_M$. Also, the number of set elements in each proper subset $S_m$ is the number $V_m \times C \times R$ which is the multiplication of the number of views $V_m$ to be imaged in the respective positions of bed 4, the number of channels C of the detector 12 and the number of rows R of the detector 12.

Therefore, in each proper subset $\{S_1, \ldots, S_m, \ldots, S_M\}$, $S_1=\{1, 2, \ldots, V_1 \times C \times R\}$, $S_2=\{V_1 \times C \times R+1, \ldots, V_1 \times C \times R + V_2 \times C \times R\}$, $\ldots$, $S_m=\{(V_1+V_2+ \ldots +V_{m-1}) \times C \times R+1, \ldots, (V_1+V_2+ \ldots +V_{m-1}+V_m) \times C \times R\}$, $\ldots$, $S_M=\{(V_1+V_2+ \ldots +V_{M-1}) \times C \times R+1, \ldots, (V_1+V_2+ \ldots +V_{M-1}+V_M) \times C \times R\}$.

For example, in each position of the bed 9, a view for one revolution (360°) is constantly imaged, and the number of views per revolution (=360°) is set as $V_{360}$. In this case, $V_1 = \ldots = V_m = \ldots = V_M = V_{360}$, the number of set elements in each proper subset $S_m = V_{360} \times C \times R$, and the number of set elements in the entire proper subset $S_m$ becomes the same.

Next, a case of helical scanning will be described. In case of helical scanning, the arithmetic device 5 determines the number of set elements included in proper subset $S_m$ based on the number of views defined as the calculation unit of the back projection process in the iterative approximation method, i.e. the number of back projection views. This is because the arithmetic device 5 needs to determine each proper subset $S_m$ for acquiring the projection data necessary for creating a piece of cross-sectional image as a set element.

For example, in the case that an iterative approximation process is implemented by the method disclosed in Non-patent Document 5, the number of back projection views equals the value in which phase width tw of the back projection (referred to as "back projection phase width tw") is multiplied by the number of scanning views $V_d$ per revolution which is set as the scanning condition.

In back projection phase width tw, the value which indicates the phase for one revolution (=360°) is 1, the value which indicates the phase for half a revolution (=180°) is ½, the value which indicates the phase for two revolutions (~720°) is 2, and so on.

Here, back projection phase width tw is an arbitrary parameter, which is empirically determined in Non-patent Document 5 in accordance with the bed-feeding velocity and the size of a reconstructed image.

Thus it is preferable that the arithmetic device 5 stores back projection phase width tw in the storage device 8 in advance for each bed-feeding velocity and the reconstructed image size. Then the arithmetic device 5 obtains from the storage device 8 a single back projection phase width tw corresponding to the bed-feeding velocity set as a scanning condition and the reconstructed image size set as a reconstruction condition. Next, the arithmetic device 5 sets the value in which the number of scanning views $V_d$ per revolution which is set as the scanning condition is multiplied by back projection phase width tw obtained from the storage device 8 as the number of back projection views.

In a case in which an operator puts a high priority on the calculation velocity, the proper subset may also be determined by replacing the number of back projection views as half a revolution (the minimum unit of back projection). Meanwhile, the value of the reconstruction condition is to be applied to the back projection process without depending on the replacement.

In case of helical scan, the number of partitions in universal set Ω, i.e. the number M of proper subsets $S_m$ is the quotient in which the number of views V in an entire scanning is divided by the number of back projection views $tw \times V_d$. When the number of views V in an entire scanning is aliquant by the number of back projection views $tw \times V_d$, the remaining views are to be included in the last proper subset $S_M$.

The number of set elements in all proper subsets $S_m$ is the same, which is the number $tw \times V_d \times C \times R$ which is the multiplication of back projection phase width tw, the number of scanning views $V_d$ per revolution, the number of channels C and the number of rows R.

Therefore, in each proper subset $\{S_1, \ldots, S_m, \ldots, S_M\}$, $S_1=\{1, 2, \ldots, tw \times V_d \times C \times R\}$, $S_2=\{tw \times V_d \times C \times R+1, \ldots, 2 \times tw \times V_d \times C \times R\}$, $\ldots$, $S_m=\{(m-1) \times tw \times V_d \times C \times R+1, \ldots, m \times tw \times V_d \times C \times R\}$, $\ldots$, $S_M=\{(M-1) \times tw \times V_d \times C \times R+1, \ldots, M \times tw \times V_d \times C \times R\}$.

The description will be returned to the explanation of FIG. 5. Next, arithmetic 5 calculates the weight related to a penalty term the penalty-term weight) $\{\beta_1, \ldots, \beta_m, \ldots, \beta_M\}$ for each proper subset $S_m$ determined in step 2 on the basis of detector output weight $d_i$ corresponding to the set elements included in proper subset $S_m$ (step 3). The detail of the penalty-term weight calculation process will be described below referring to FIG. 6~FIG. 8.

Next, the arithmetic device 5 executes the iterative approximation method with respect to $i \in S_m$ using penalty-term weight $\beta_m$ for each proper subset $S_m$ (step 4). In other words, the arithmetic device 5 executes the iterative approximation projection data correcting process while changing penalty-term weight $\beta_m$ for each region. The following equation is an example of an evaluation function.

[Equation 3]

$$\Phi(x) = \sum_{i=1}^{I} d_i (y_i - p_i)^2 + \sum_{m=1}^{M} \beta_m \sum_{i \in S_m} \sum_{k \in \kappa_i} v_{ik} \psi(p_i - p_k) \quad (3)$$

Here, since the numerical analytical approach of the present invention is to change the penalty-term weight in an evaluation function for each region, the present invention can be applied without depending on the numerical analytical method to be used for optimization as long as the evaluation function includes a detector output weight and a penalty term.

The deviation of an updating equation in the iterative approximation method from the equation (3) can be performed by a commonly-known method. For example, an updating equation can be deviated by using the Gauss-Seidel method as disclosed in Non-patent Document 6.

The arithmetic device 5 deviates an updating equation in the iterative approximation method from the equation (3), substitutes calculated detector output weight $d_i$ and penalty-term weight for each proper subset $S_m$ into the deviated updating equation, and performs the projection data correcting process using the iterative approximation method.

In the following description, two kinds of penalty-term weight calculation processes will be described in detail referring to FIG. 6~FIG. 8. The first penalty-term calculation process will be described referring to FIG. 6 and FIG. 7. The second penalty-term calculation process will be described referring to FIG. 8.

An operator can arbitrarily select either the process considering a desired calculation time or estimation accuracy of the penalty-term weight.

First, the first penalty-term weight calculation process will be described.

In the first penalty-term weight calculation process, the arithmetic device 5 previously stores, for each noise reducing rate, in the storage device 8 the penalty-term weight value of which the noise reducing rate being comparable to that of the reference phantom is achieved (hereinafter referred to as "penalty-term weight reference value").

For example, the arithmetic device 5 stores in the storage device 8 the noise reducing rate table in which penalty-term weight reference values $\beta^*_{10}$, $\beta^*_{20}$, $\beta^*_{30}$, . . . are registered with respect to noise reducing rates 10%, 20%, 30%, . . . in advance. Penalty-term weight reference values $\beta^*_{10}$, $\beta^*_{20}$, $\beta^*_{30}$, . . . are set as the values acquired by actually scanning a reference phantom which is an orbicular water phantom or a simulation of a human body and performing an image reconstruction process.

Then the arithmetic device 5 acquires the penalty-term weight reference value corresponding to the input noise reducing rate from the storage device 8. Next, the arithmetic device 5 calculates the representative value for each proper subset $S_m$ on the basis of detector output weight $d_i$ corresponding to the set elements included in each proper subset $S_m$. Next, the arithmetic device 5 sets the value which is the multiplication of the representative value for each proper subset $S_m$ and the penalty-term weight reference value acquired from the storage device 8 as penalty-term weight $\beta_m$ for each proper subset $S_m$.

In particular, it is preferable that the arithmetic device 5 sets, for each proper subset $S_m$, anyone of three values that are the average value and the central value of detector output weight $d_i$ corresponding to the set elements included in proper subset $S_m$ as well as the class for segmenting an entire histogram categorized by detector output weight $d_i$ by a predetermined proportion, as the representative value for each proper subset $S_m$.

Figure 6:
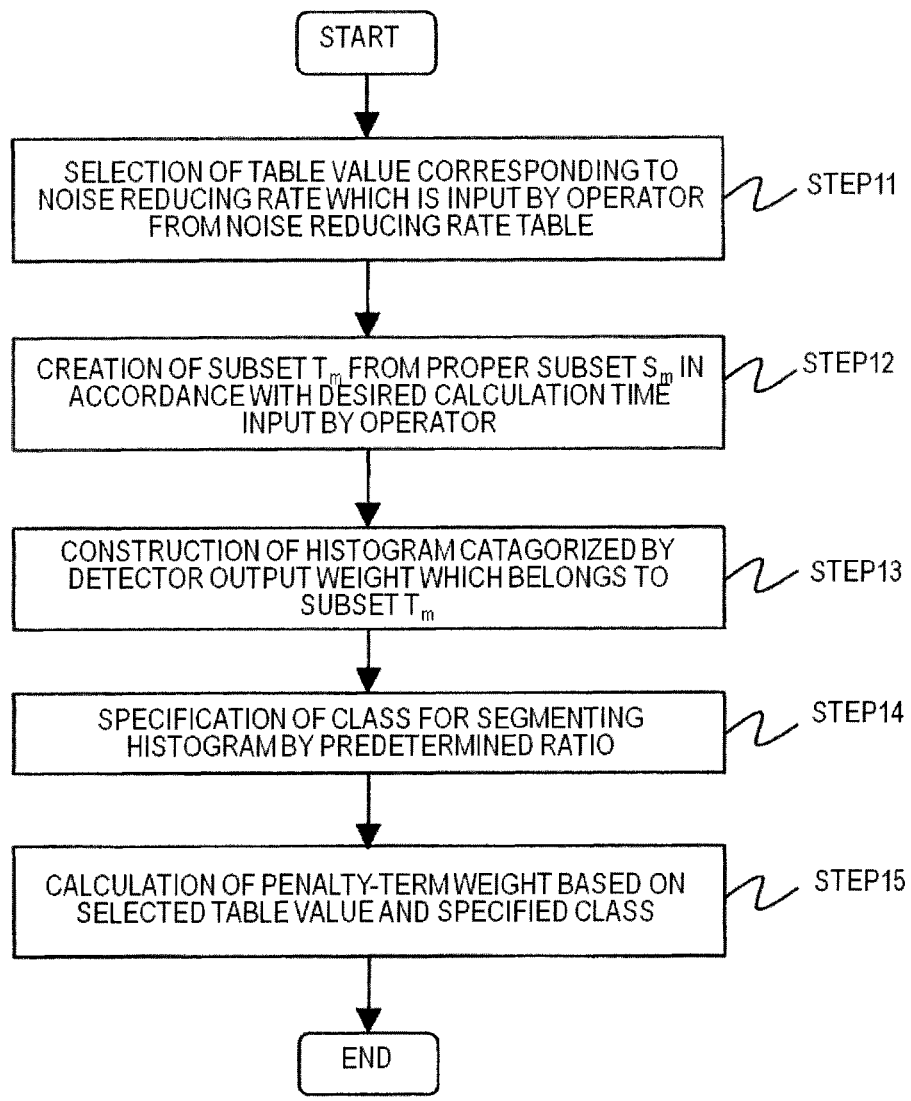
FIG. 6 is a flowchart showing the calculation process of a first penalty-term weight.

The flowchart in FIG. 6 shows a case in which the class for segmenting an entire histogram categorized by detector output weight $d_i$ is calculated as the representative value.

Also, while the calculation process of penalty-term weight $\beta_m$ is indicated with respect to proper subset $S_m$ in the flowchart of FIG. 6, it is the same in the other proper subsets.

As shown in FIG. 6, the arithmetic device 5 selects the table value corresponding to a desired noise reducing rate input by an operator from the noise reducing rate table stored in the storage device 8 (step 11).

Next, the arithmetic device 5 creates subset $T_m$ of proper subset $S_m$ from the set elements included in proper subset $S_m$ in accordance with a desired calculation time input by the operator (step 12).

The arithmetic device 5 creates subset $T_m$ by thinning the set elements included in $S_m$ on the basis of a previously defined thinning rule.

As for the thinning rule, for example, the views can be thinned alternately. By doing so, the image quality of the ultimately created cross-sectional image will be less likely to be affected. For example, when the views are obtained for every 1° in the revolution direction, the number of scanning views $V_d$ per revolution becomes 360. By alternately thinning 360 views, 180 views remain and the number of set elements in subset $T_m$ becomes a half of the number of set elements in proper subset $S_m$.

Also for example, thinning the far left channel and the far right channel in each view can be considered as a thinning rule. This is because the far left channel and the far right channel in each view often receive an X-ray which does not pass through an object and the image quality of an ultimately created cross-sectional image is less likely to be affected. For example, with respect to the number of channels C, by thinning 10% of data from the far left channel and the 10% of data from the far right channel, the number of set elements in subset $T_m$ becomes ⅘ of the set elements in proper subset $S_m$.

The above-described different thinning rules can also be combined.

In any thinning rule (or combination of plural thinning rules), it is possible to adjust the amount of thinning in accordance with a desired calculation time which is input by an operator. In this manner, calculation time can be adjusted according to the intention of an operator by creating subset $T_m$ of proper subsets $S_m$ and performing a process to be described below on subset $T_m$.

Next, the arithmetic device 5 constructs a histogram categorized by detector output weight $d_i$ corresponding to the set elements of subset $T_m$ created in step 12 (step 13). Here, any known method can be used as the method for calculating detector output weight $d_i$. For example, as disclosed in Non-patent Document 6, the arithmetic device 5 may also calculate detector output weight $d_i$ by subjecting projection data to logarithmic inverse conversion then multiplying the converted data by air data.

Figure 7:
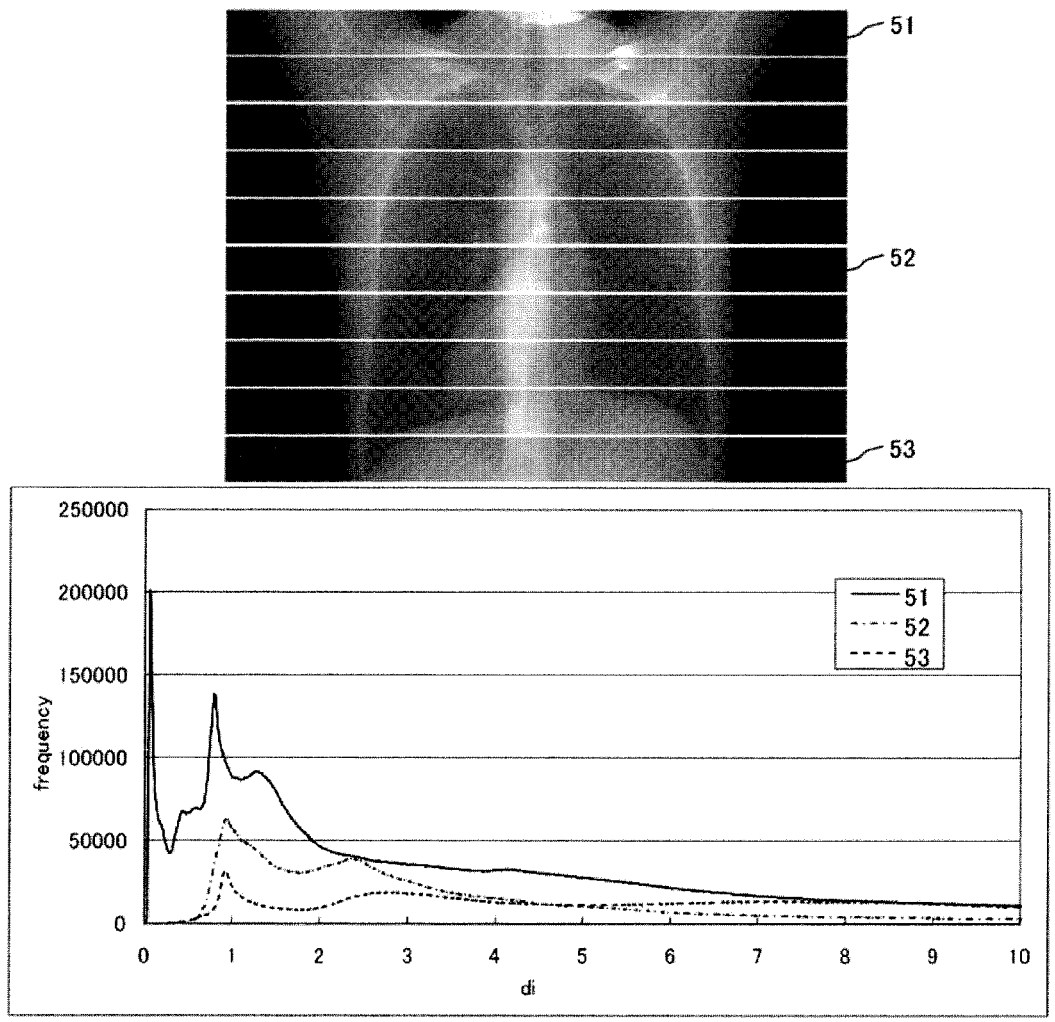
FIG. 7 is a view showing an example of a histogram.

FIG. 7 shows an example of a histogram. The histogram shown in FIG. 7 has the horizontal axis (class) which indicates detector output weight $d_i$ and the vertical axis (frequency) which indicates the number of set elements corresponding to detector output weight $d_i$ equal to the value of each class.

A histogram shows different distributions depending on the size or region of an object, which is an index to represent the characteristics of the regions in the object.

The histogram of a shoulder region 51 has its maximum peak where the value of the class is near 0. Also, the overall values of detector output weight $d_i$ are low in the histogram of the shoulder region 51. This is because the shoulder region 51 includes many bone regions in which a large amount of X-ray is reduced.

Also, the histogram of a chest region 52 and an abdominal region 53 have their maximum peaks where the value of the class is near 1. When the histograms of the chest region 52 and the abdominal region 53 are compared, the frequency of the classes 1~3 is: the histogram of the chest region 52>the histogram of the abdominal region 53, and the frequency of the classes above 5 is: the histogram of the chest region 52<the histogram of the abdominal region 53. This is because the chest region 52 includes lungs of which the attenuation amount of X-rays is small.

The histogram shown in FIG. 7 also represents the characteristic of the size of an object as well, since the class at which the maximum peak exists changes depending on the size of the object.

The explanation returns to FIG. 6. Next, the arithmetic device 5 calculates the area of each histogram shown in FIG. 7, and specifies the class for segmenting the area of the histogram into a predetermined proportion as the representative value (step 14). In addition, the representative value may also be the central value or the average value of detector output weight $d_i$ included in $i \in S_m$ as previously described. An operator can arbitrarily select the representative value.

Next, the arithmetic device 5 calculates the penalty-term weight $\beta_m$ of proper subset $S_m$ by multiplying the table value selected in step 11 by the class (representative value) specified in step 14 (step 15).

The calculation process of the first penalty-term weight does not require complicated calculations, thus penalty-term weight $\beta_m$ of proper subset $S_m$ can be calculated without drastically increasing the amount of calculation.

Next, the calculation process of the second penalty-term weight will be described. The calculation process of the second penalty-term weight is based on the knowledge as follows.

(1) In a case in which the detector output weight is set as a constant and the iterative approximation method is executed by an arbitrary penalty-term weight, it is empirically evident that approximately the same noise reducing rate can be obtained without depending on an object and a region.
(2) There is a high correlation between the correction amount of a projection value (pixel value) by the iterative approximation method and the noise reducing rate.

The above-described knowledge can be applied to both of the iterative approximation projection data correcting process and the iterative approximation reconstructing process.

Using the above-described knowledge, in the second penalty-term weight calculation method, the arithmetic device 5 substitutes detector output weight $d_i$ corresponding to the set elements included in proper subset $S_m$ and the projection data into the correction amount calculating function which calculates the correction amount of the projection data in a case in which the iterative approximation method is executed. Here, penalty-term weight $\beta_m$ for each proper subset $S_m$ is included in the correction amount calculating function as a variable. Then the arithmetic device 5 determines penalty-term weight $\beta_m$ for each proper subset $S_m$ so as to minimize the error in the value of the correction amount calculating function (=summation of the correction amount of projection data) and a predetermined correction amount reference value (=the reference value of the summation of the correction amount in projection data).

The determination process of a predetermined correction amount reference value is as follows. The arithmetic device 5, as in the calculation process of the first penalty-term weight, stores a noise reducing rate table in the storage device 8, and obtains the penalty-term weight reference value corresponding to the input noise reducing rate from the storage device 8. Then the arithmetic device 5 sets the detector output weight as a constant, calculates the correction amount of projection data in a case wherein the iterative approximation method is executed using the penalty-term weight reference value obtained from the storage device 8, and sets the calculated correction amount as a predetermined correction amount reference value.

The second penalty-term weight calculating process will be described below in detail referring to FIG. 8. While the calculation process of penalty-term weight $\beta_m$ is shown in the flowchart of FIG. 8 with respect to proper subset $S_m$, the same process can also be applied to the other proper subsets.

Figure 8:
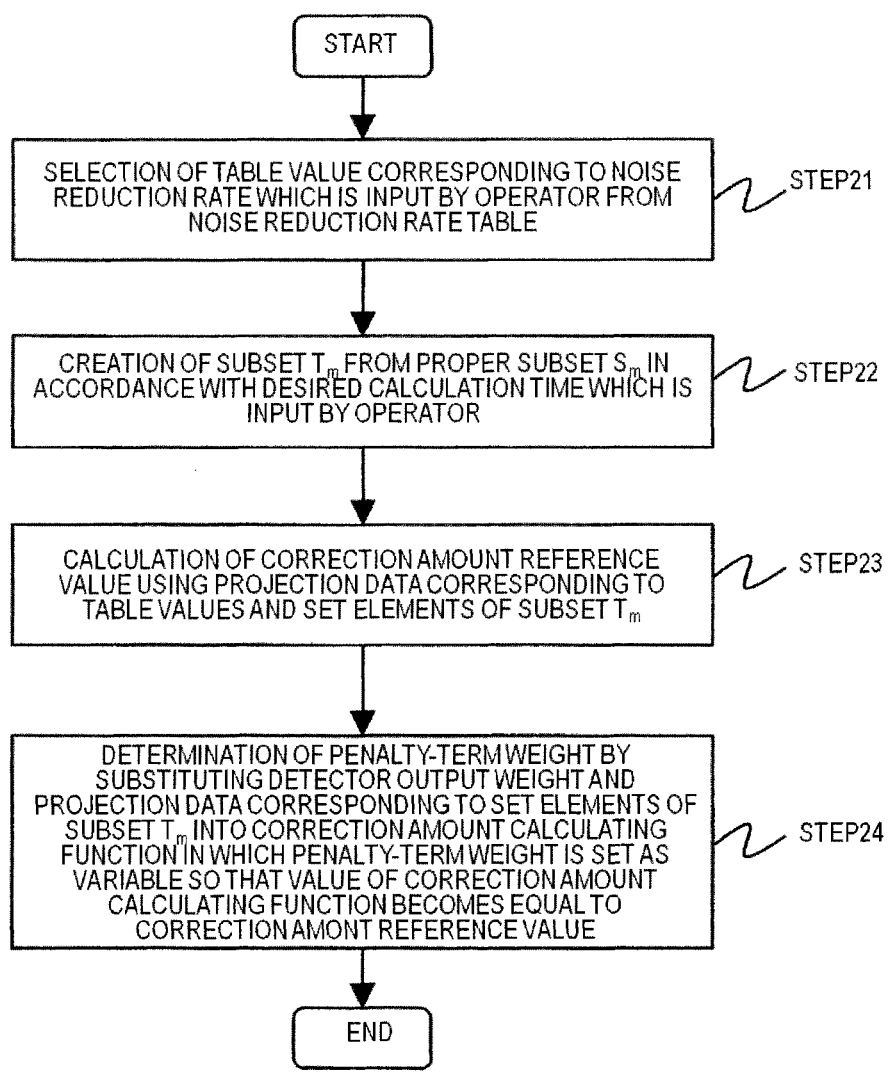
FIG. 8 is a flowchart showing the calculation process of a second penalty-term weight.

As shown in FIG. 8, the arithmetic device 5 selects the table value corresponding to the noise reducing rate input by an operator from the noise reducing rate table stored in the storage device 8 (step 21). In addition, the noise reducing table to be used for calculating the first penalty-term weight and the noise reducing rate table to be used for calculating the second penalty-term weight have different stored table values due to the difference in the processing content.

Next, the arithmetic device 5 creates subset $T_m$ of proper subset $S_m$ from the set elements included in proper subset $S_m$ in accordance with a desired calculation time input by the operator (step 22). The creation process of subset $T_m$ is the same as in step 12.

Next, the arithmetic device 5 estimates the projection value after applying the iterative approximation projection data correcting process by setting detector output weight $d_i$ as an arbitrary constant, using the table value selected in step 21 and the projection data corresponding to the set elements of subset $T_m$ created in step 22. Here, since it is difficult to analytically calculate a projection value after being applied from the viewpoint of the calculation amount and the memory required for the calculation, an approximation value is used as a substitute. By assuming that the focused projection value is calculated only from the adjacent channels, rows and views, the approximation value can be easily calculated. The approximation value may also be calculated by replacing the back matrix necessary for calculation of the projection value after iteration into an approximate matrix using a known method. Then the arithmetic device 5 calculates the error of the approximation value and the projection value in the iterative approximation projection data correcting process before application, and sets the summation of the errors as the correction amount reference value (step 23). A commonly-known index such as an absolute error or mean square error can be used for the error calculation process here.

Next, the arithmetic device 5 substitutes the correction amount calculating function having a variable of penalty-term weight $\beta_m$ with detector output weight $d_i$ and the projection data corresponding to the set elements of subset $T_m$ created in step 23. Then the arithmetic device 5 determines the penalty-term weight so that the value of the correction amount calculating function equals to the correction amount reference value calculated in step 23 (step 24). Here, a commonly-known numerical analytical approach (for example, the bisection method) can be applied to minimize the error in the correction amount calculating function and the correction amount reference value.

The calculation process of the second penalty-term weight is based on the previously described knowledge, thus penalty-term weight $\beta_m$ of proper subset $S_m$ can be calculated with high accuracy.

As described above, in accordance with Embodiment 1, it is possible to achieve the noise reducing effect in CT images as is conventionally done in the iterative approximation projection data correcting process by setting penalty-term weight $\beta_m$ to be used in the iterative approximation data correcting process as a constant in proper subset $S_m$.

Also, the variability of the noise reducing effect among plural regions can be suppressed by calculating penalty-term weight $\beta_m$ for each proper subset $S_m$ on the basis of the detector output weight $d_i$ and the projection value to which the information of an object is reflected.

Embodiment 2

Embodiment 2 will be described below. In Embodiment 2, a case in which the present invention is applied to the iterative approximation reconstructing process will be described. That is, the arithmetic device 5 executes an image reconstruction process in Embodiment 2 using the iterative approximation method in which the detector output weight and the penalty-term weight are included in an evaluation function.

The difference from Embodiment 1 is only that the equation (3) in Embodiment 1 changes to the following equation.

Embodiment 4

$$\Phi(x) = \sum_{m=1}^{M} \frac{1}{\beta_m} \sum_{i \in S_m} d_i \left( y_i - \sum_{j=1}^{J} a_{ij} x_j \right)^2 + \sum_{j=1}^{J} \sum_{k \in X_j} w_{jk} \psi(x_j - x_k) \quad (4)$$

As is in the equation (3), the updating equation in the iterative approximation method can be developed from the equation (4). The arithmetic device 5 substitutes the detector output weight $d_i$ which is calculated in the same manner as in Embodiment 1 and penalty-term weight $\beta_m$ for each proper subset $S_m$ into the developed updating equation, and executes the image reconstruction process using the iterative approximation method.

As described above, in Embodiment 2, the noise reducing effect in CT images can be achieved as is conventionally done in the iterative approximation reconstructing process by setting penalty-term weight $\beta_m$ to be used in the iterative approximation reconstructing process as a constant in proper subset $S_m$ as in Embodiment 1.

Also, the variability of noise reducing effect among regions can be suppressed by calculating penalty-term weight $\beta_m$ for each proper set $S_m$ on the basis of detector output weight $d_i$ and the projection value to which the information of an object is reflected as in Embodiment 1.

Embodiment 3

Embodiment 3 will now be described. In Embodiment 3, a case to which the present invention is applied to both the iterative approximation projection data correcting process and the iterative approximation reconstructing process will be described. That is, in Embodiment 3, the arithmetic device 5 executes the projection data correcting process and the image reconstruction process using the iterative approximation method in which a detector output weight and a penalty term are included in an evaluation function.

Embodiment 3 is the combination of Embodiment 1 and Embodiment 2. More specifically, the arithmetic device 5 develops an updating equation in the iterative approximation method from the equation (3), substitutes detector output weight $d_i$ and penalty-term weight $d_i$ for each proper subset $S_m$ which are calculated as in Embodiment 1 into the developed updating equation, and performs the correcting process of the projection data using the iterative approximation method as in Embodiment 1. The arithmetic device 5 also develops an updating equation in the iterative approximation method from the equation (4), substitutes detector output weight $d_i$ and penalty-term weight $\beta_m$ for each proper subset $S_m$ calculated as in Embodiment 1 into the developed updating equation, and performs the image reconstruction process using the iterative approximation method, as in Embodiment 2.

As described above, in Embodiment 3, the noise reducing effect in CT images can be achieved as is conventionally done in the iterative approximation projection data correcting process and the iterative approximation reconstructing process by setting penalty-term weight $\beta_m$ to be used in the iterative approximation projection data correcting process and the iterative approximation reconstructing process as a constant in proper subset $S_m$.

Also, the variability of noise reducing effect among regions can be suppressed by calculating penalty-term weight $\beta_m$ for each proper set $S_m$ on the basis of detector output weight $d_i$ and the projection value to which the information of an object reflected.

The preferable embodiments of the medical image processing device, etc. related to the present invention have been described referring to the attached drawings. However, the present invention is not limited to these embodiments. It is obvious that persons skilled in the art can make various kinds of alterations or modifications within the scope of the technical idea disclosed in this application, and it is understandable that they belong to the technical scope of the present invention.

DESCRIPTION OF REFERENCE NUMERALS

1 X-ray CT apparatus
4 bed
5 arithmetic device
6 input device
7 display device
8 storage device
11 X-ray tube
12 detector
41 cross-sectional image
42 channel
43 coronal cross-sectional image
44 row
45 scan direction

The invention claimed is:

1. A medical image processing device configured to execute at least one of (i) a projection data correcting process and (ii) an image reconstruction process, using an iterative approximation method in which a detector output weight which is a weight in accordance with an output of a detector and a penalty-term are included in an evaluation function, comprising:
    a proper subset determining unit configured to determine one or more proper subsets, on the basis of scanning conditions and reconstruction conditions, from a universal set of which the information for uniquely specifying combination of a channel of the detector, a row of the detector and a view which is the acquisition unit of the projection data is a set element;
    a penalty-term weight calculating unit configured to calculate, for each of the proper subsets, a penalty-term weight which is a weight multiplied to the penalty term on the basis of the detector output weight corresponding to the set element included in the proper subset; and
    an iterative approximation method executing unit configured to execute the iterative approximation method using the penalty-term weight for each of the proper subsets.

2. The medical image processing device according to claim 1, wherein the proper subset determining unit determines, in case of helical scan, the number of the set elements included in the proper subset based on the number of back projection views which is the number of the views defined as an accounting unit for a back projection process in the iterative approximation method.

3. The medical image processing device according to claim 2, wherein the proper subset determining unit:
    stores in advance in a storage device the back projection phase width which is a phase width of a back projection process in the iterative approximation method for each bed translation velocity and each size of the reconstruction image;
    acquires from the storage device the back projection phase width corresponding to bed translation velocity set as the scanning condition and size of the reconstruction image set as the reconstruction condition; and
    sets a value in which the number of scanning views per revolution set as the scanning condition is multiplied by the back projection phase width acquired from the storage device as the number of back projection views.

4. The medical image processing device according to claim 1, wherein the penalty-term weight calculating unit:
    stores in advance in the storage unit, for each noise reducing rate, a penalty-term weight reference value which is the penalty-term weight by which the noise reduction comparable to that of the noise reducing rate is achieved with respect to a reference phantom;

acquires the penalty-term weight reference value corresponding to the input noise reducing rate from the storage device;

calculates, for each of the proper subsets, a representative value on the basis of the detector output weight corresponding to the set elements included in the proper subset; and sets the value in which the representative value for each of the proper subsets is multiplied by the penalty-term weight reference value acquired from the storage unit as the penalty-term weight for each of the proper subset.

5. The medical image processing device according to claim 4, wherein the penalty-term weight calculating unit sets, for each of the proper subsets, any one of three values which are the average value and the central value of the detector output weight corresponding to the set elements included in the proper subset as well as the class for dividing an entire histogram categorized by the detector output weight by a predetermined proportion, as the representative value for each of the proper subsets.

6. The medical image processing device according to claim 1, wherein the penalty-term weight calculating unit determines the penalty-term weight for each of the proper subsets so that the error between a value which is calculated by substituting the correction amount calculating function which calculates the correction amount of the projection data when the penalty-term weight for each of the proper subsets is variable and the iterative approximation method is executed into the detector output weight and the projection data corresponding to the set elements included in the proper subset and a correction amount reference value is minimized.

7. The medical image processing device according to claim 6, wherein the penalty-term weight calculating unit:

stores, in the storage device in advance for each noise reducing rate, a penalty weight reference value which is the penalty-term weight by which the noise reducing effect comparable to that of the noise reducing rate is achieved with respect to a reference phantom;

acquires, from the storage device, the penalty-term weight reference value corresponding to the noise reducing rate to be input; and calculates the correction amount of the projection data in a case in which the detector output weight is a constant and the iterative approximation method is executed using the penalty-term weight reference value acquired from the storage device, so as to set the calculated correction amount as the correction amount reference value.

8. A medical image processing method which executes at least one of (i) a projection data correction process and (ii) an image reconstruction process using an iterative approximation method in which the detector output weight which is a weight in accordance with an output of a detector and a penalty term are included in an evaluation function, including:

determining, on the basis of scanning conditions and reconstruction conditions, one or more proper subsets from the universal set of which the information for uniquely specifying combination of a channel of the detector, a row of the detector and a view which is the acquisition unit of the projection data is a set element;

calculating, for each of the proper subsets, a penalty-term weight which is a weight multiplied to the penalty term on the basis of the detector output weight corresponding to the set elements included in the proper subset; and executing the iterative approximation method for each of the proper subsets using the penalty-term weight.

9. The medical image processing method according to claim 8, wherein the proper subsets are subsets of the projection data determined from the universal set of the projection data.

10. The medical image processing device according to claim 1, wherein the proper subsets are subsets of the projection data determined from the universal set of the projection data.

* * * * *